Aug. 10, 1971 F. W. ANDERSON Plant Pat. 3,062
APRICOT TREE
Filed Sept. 8, 1969
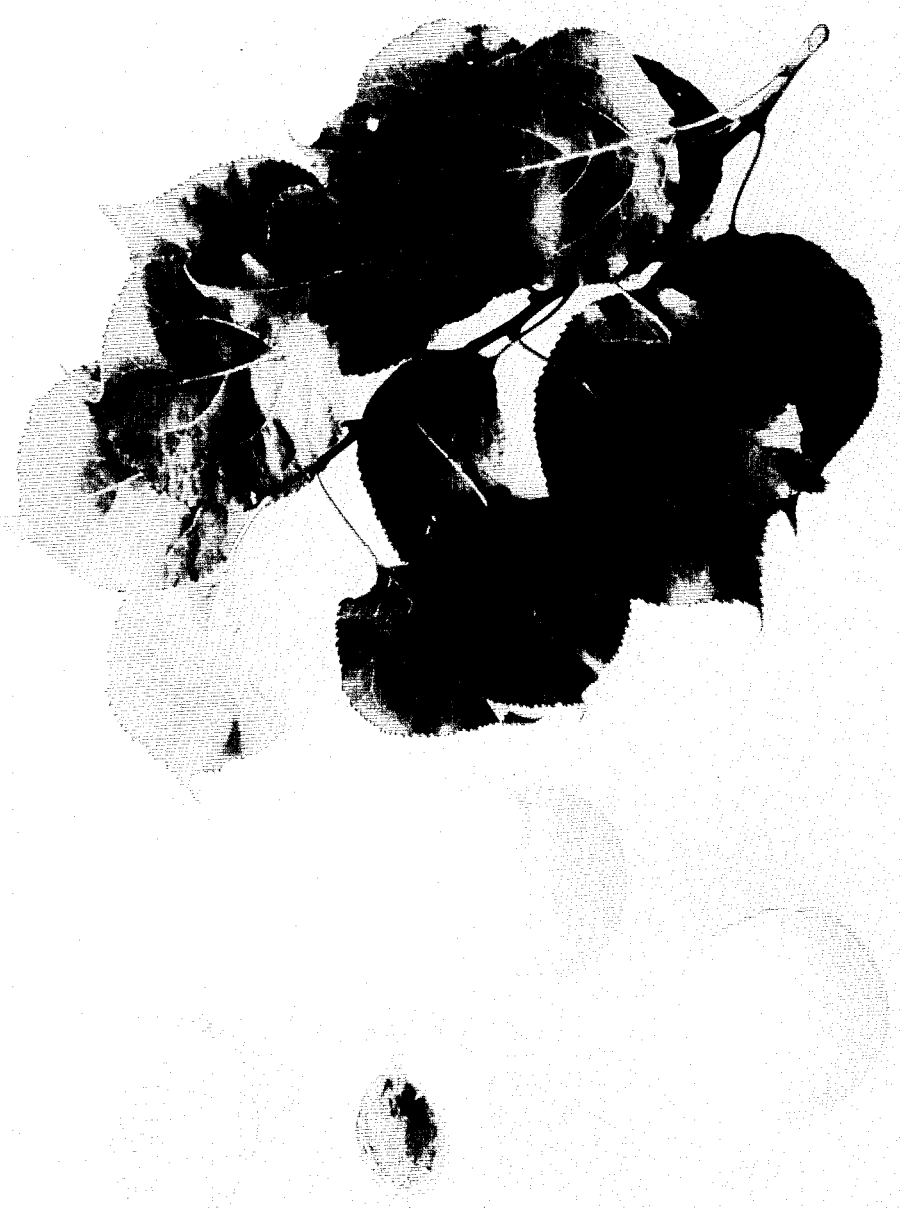
INVENTOR
Frederic W. Anderson
BY
Webster & Webster
ATTORNEYS

United States Patent Office

Plant Pat. 3,062
Patented Aug. 10, 1971

3,062
APRICOT TREE

Frederic W. Anderson, Merced, Calif., assignor to The Burchell Nursery, Inc., Modesto, Calif.

Filed Sept. 8, 1969, Ser. No. 856,224
Int. Cl. A01h 5/03
U.S. Cl. Plt.—39 1 Claim

ABSTRACT OF THE DISCLOSURE

An apricot tree which is of large to medium size, vigorous, spreading, open, and a regular and productive bearer of large to medium size freestone fruit having an average larger size, tougher skin, firmer flesh, and less pit burn than the fruit of the Blenheim (unpatented), long the leading commercial variety of apricot tree grown in the State of California; the fruit of the present variety ripening later than the Modesto (United States Plant Patent No. 2,543) and Patterson (United States Plant Patent No. 2,877).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of apricot tree resulted from my endeavors in the conduct of such plant breeding program.

ORIGIN OF THE VARIETY

The present variety of apricot tree was originated by me in my experimental nursery and orchard, located as aforesaid, as a second generation seedling of the Perfection (unpatented). When such seedling (which was maintained under careful and continuing observation) bore fruit, I recognized its novel characteristics, and, therefore, undertook asexual reproduction of it preparatory to subsequent introduction to the trade.

ASEXUAL REPRODUCTION OF THE VARIETY

Asexual reproduction of the present variety of apricot tree was accomplished by me in my aforementioned experimental orchard by top-working on mature orchard trees, and all such reproductions ran true to the original tree in every respect.

SUMMARY OF THE VARIETY

The present variety of apricot tree is characterized by large to medium size; by vigorous, spreading, and open growth; and by regular and productive bearing of large to medium size freestone fruit having an average larger size, tougher skin, firmer flesh, and less pit burn than the fruit of the Blenheim.

The fruit of the present variety of apricot tree is—by virtue of the characteristics described in the preceding paragraph—more adaptable, in comparison to the Blenheim, to mechanical harvesting, processing, and packaging.

The present variety of apricot tree is further characterized by a harvest period which, on the average, is approximately six days after the Modesto and approximately three days after the Patterson. This extension of the harvest period is of obvious substantial advantage to commercial processors of the fruit.

BRIEF DESCRIPTION OF THE DRAWING

The drawing is an illustration, by photographic reproduction in color, of a twig with leaves, and detached fruit; one of the latter being cut into halves to expose the flesh, and with the stone remaining in place in one of such halves.

DESCRIPTION OF THE VARIETY

The botanical details of this new and distinct variety of apricot tree—with color definitions referenced to Maerz and Paul Dictionary of Color—are as follows:

Tree:
- *Size.*—Large to medium.
- *Vigor.*—Vigorous.
- *Growth.*—Spreading.
- *Density.*—Open.
- *Production.*—Productive.
- *Bearing.*—Regular bearer.

Trunk:
- *Size.*—Medium.
- *Texture.*—Medium.

Branches: Size.—Medium; Texture.—Medium.
- *Lenticels.*—Number—medium; Size—medium.

Leaves:
- *Size.*—Large; average length—3"; average width—2½".
- *Form.*—Cordate; acutely pointed.
- *Thickness.*—Thick.
- *Texture.*—Smooth.
- *Margin.*—Coarsely serrate.
- *Petiole.*—Length—medium, thickness—medium.
- *Glands.*—Average number—usually 4 on petiole, and 2 on blade; alternate; medium size; globose; position—those on the petiole are on the half thereof adjacent the blade.
- *Color.*—Top side—medium green (23–L–10); under side—lighter green (22–K–8).

Flower buds:
- *Size.*—Medium.
- *Form.*—Obtuse.

Flowers:
- *Blooming Period.*—Feb. 27 to Mar. 9, 1969; approximately with Blenheim.
- *Size.*—Medium.
- *Color.*—White at full bloom.

Fruit:
- *Maturity when described.*—Eating ripe—July 3, 1969.
- *Date of first picking.*—June 28, 1969.
- *Date of last picking.*—July 10, 1969.
- *Size.*—Uniform to variable; large to medium—average larger than Blenheim; average diameter axially—1⅞"; average transversely in suture plane—1¾".
- *Form.*—Globose; compressed laterally.
- *Suture.*—Distinct; extends from base to apex.
- *Ventral surface.*—Rounded strongly.
- *Cavity.*—Average depth—1¼"; average breadth—⅝".
- *Base.*—Rounded; oblique.
- *Apex.*—Short; depressed.
- *Pistil point.*—Minute.

Skin:
- *Thickness.*—Medium.
- *Texture.*—Tough—more so than Blenheim.
- *Tendency to crack.*—Slight.
- *Down.*—Scant.
- *Color.*—Apricot yellow (10–J–7 to 10–K–8).

Flesh:
- *Juice.*—Moderate; rich.
- *Texture.*—Very firm—firmer than Blenheim; meaty.
- *Fibers.*—Few.
- *Ripens.*—Evenly.
- *Flavor.*—Subacid; vinous.
- *Aroma.*—Distinct.

*Eating quality.*—Good to best.

*Color.*—Apricot yellow (10–K–9); surface of pit cavity—yellow.

Stone:

*Type.*—Free.

*Fibers.*—Short.

*Size.*—Medium; average length—1″; average breadth ¾″; average thickness—5/16″.

*Form.*—Oval.

*Base.*—Straight.

*Apex.*—Rounded.

*Sides.*—Equal.

*Ventral edge.*—Thick.

*Dorsal edge.*—Narrow, with shallow narrow groove toward base.

*Tendency to split.*—None.

*Color.*—Brown (8–H–8).

Use: Market—local; dessert; canning; drying; freezing.

Keeping quality: Good—extremely long shelf life.

Resistance to insects and diseases: No unusual susceptibilities noted.

Shipping quality: Very good.

The apricot tree and its fruit herein described may vary in slight detail due to climatic and soil conditions under which the variety may be grown; the present description being of the variety as grown in the Central Valley of California.

I claim:

1. A new and distinct variety of apricot tree, substantially as illustrated and described, which is of large to medium size, vigorous, spreading, open, and a regular and productive bearer of large to medium size freestone fruit characterized, in comparison to the Blenheim, by an average larger size, tougher skin, firmer flesh, and less pit burn; the harvest period of the fruit being, on the average, approximately six days after the Modesto and approximately three days after the Patterson, and the fruit having an extremely long shelf life.

No references cited.

ROBERT E. BAGWILL, Primary Examiner